United States Patent [19]

Hyatt et al.

[11] Patent Number: 4,499,272

[45] Date of Patent: Feb. 12, 1985

[54] NH$_4^+$ OR GROUP IA METAL 2,7-DIMETHYL-1,2,3-TETRAHYDRO-β-HYDROXY-1-QUINOLINEPROPANESULFONATES

[75] Inventors: John A. Hyatt; Clarence A. Coates, Jr., both of Kingsport, Tenn.

[73] Assignee: Eastman Kodak Company, Rochester, N.Y.

[21] Appl. No.: 409,798

[22] Filed: Aug. 20, 1982

[51] Int. Cl.$^3$ ............... C07C 143/58; C07D 215/36; C07D 265/28; C09B 29/44

[52] U.S. Cl. .................... 546/172; 534/768; 534/782; 260/465 E; 260/507 R; 260/509; 544/51; 544/52; 546/152; 546/159; 548/165; 560/32; 560/105; 560/254

[58] Field of Search ............... 260/509, 513 R, 205, 260/155, 152; 546/165, 172, 152

[56] References Cited

U.S. PATENT DOCUMENTS

| | | | |
|---|---|---|---|
| 2,241,769 | 5/1941 | Dickey et al. | 260/510 |
| 2,319,078 | 5/1943 | McNally et al. | 260/509 |
| 3,196,173 | 7/1965 | Willmund et al. | 260/509 X |

OTHER PUBLICATIONS

Dow, Chemical Abstracts, vol. 84, #175165u, (1976).
Tsunoo, Ber. Deut. Chem. Gesell., vol. 68, pp. 1334 to 1341, (1935).

Primary Examiner—Floyd D. Higel
Attorney, Agent, or Firm—Donald W. Spurrell; Daniel B. Reece, III

[57] ABSTRACT

2-Hydroxy-3-halo-1-propanesulfonates are reacted with certain arylamines, preferably in the presence of a base such as KOH or NaOH in one or more of ethylene glycol, propylene glycol, 2-ethoxyethanol and the like to give 2-hydroxy-3-(arylamino)-1-propanesulfonates useful as couplers for acid dyes for polyamide fibers. The present coupler products which are derivatives of aniline, tetrahydroquinoline, and benzomorpholine, have the general formulae

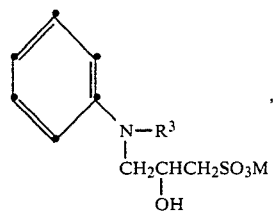

IV

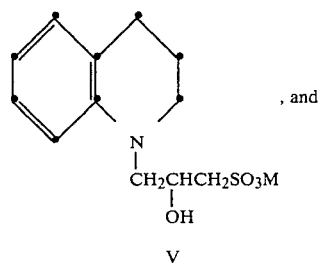

, and

V

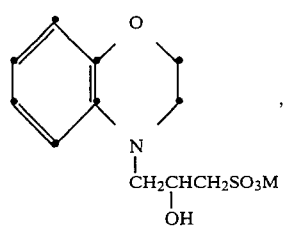

wherein the rings may be substituted with a wide variety of substituents known to the dye art;

M is NH$_4^+$ or a group IA metal, preferably Na$^+$, or K$^+$; and

R$^3$ is hydrogen or a group such as alkyl, cycloalkyl and aryl, each of which may be substituted.

1 Claim, No Drawings

NH$_4^-$ OR GROUP IA METAL 2,7-DIMETHYL-1,2,3-TETRAHYDRO-$\beta$-HYDROXY-1-QUINOLINEPROPANESULFONATES This invention concerns the reaction of an ammonium or group IA metal-2-hydroxy-3-halo-1-propanesulfonate with certain arylamines, preferably in the presence of a base such as KOH or NaOH in one or more of ethylene glycol, propylene glycol, 2-ethoxyethanol, 2-methoxyethanol, 2-butoxyethanol, and 2-propoxyethanol to produce couplers for acid dyes for polyamide fibers.

The present reaction sequence, exemplified by an aniline type compound, is as follows:

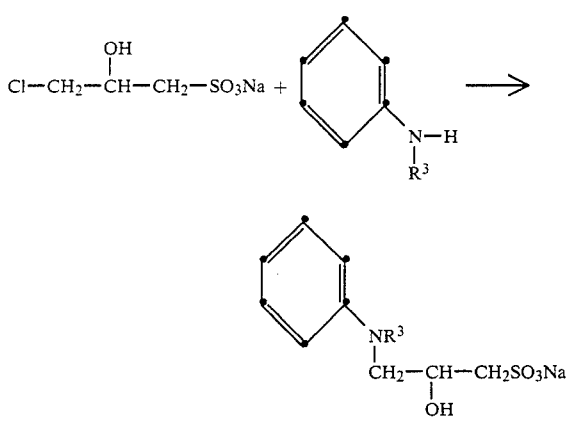

The aryl amine reactants useful herein have the formulae

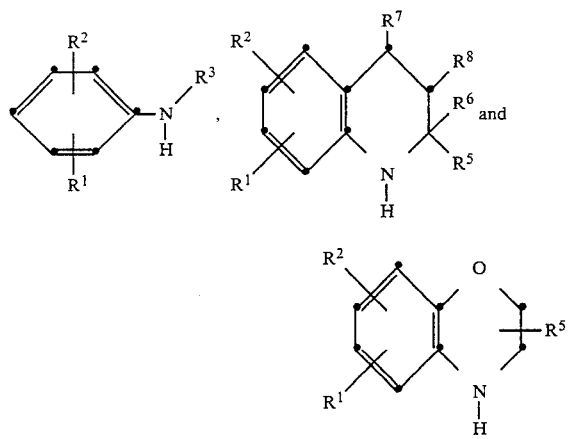

wherein

R$^1$ and R$^2$ are each selected from hydrogen, fluorine, chlorine, bromine, alkyl, cycloalkyl, alkoxy, phenoxy, alkylthio, arylthio, and radicals having the formula —NH—X—R$^9$ in which X is —CO—, —COO—, or —SO$_2$—, and R$^9$ is selected from alkyl, aryl, alkoxyaryl, cycloalkyl and alkyl substituted with halogen, hydroxy, phenoxy, aryl, cyano, cycloalkyl, alkylsulfonyl, alkylthio, alkanoyloxy, and alkoxy, and when X is —CO—, R$^9$ is also selected from hydrogen, amino, alkenyl, alkylamino, dialkylamino, arylamino and furyl;

R$^3$ is selected from hydrogen; cycloalkyl; cycloalkyl substituted with one or two groups selected from alkyl, —OH, alkoxy, halogen and hydroxy substituted alkyl; phenyl; phenyl substituted with alkyl, alkoxy, halogen, alkanoylamino, cyano or alkoxycarbonyl; straight or branched alkenyl of 2-6 carbons; and straight or branched alkyl;

wherein the alkyl, alkylene, and such moieties contained in the R$^1$, R$^2$, and R$^3$ groups may be substituted with 1-3 of the following: hydroxy; halogen; cyano; amino; alkoxy; alkoxycarbonyl substituted aroyloxy; alkoxycarbonyl substituted aryl; alkoxyalkoxy; hydroxyalkoxy; succinimido; glutarimido; phthalimido; phthalimidino; 2-pyrrolidono; cyclohexyl; phenoxy; phenyl; phenyl substituted with alkyl, alkoxy, alkoxycarbonyl, halogen, alkanoylamino or cyano; acrylamido; benzoylsulfonimido; alkenylcarbonylamino; groups of the formula

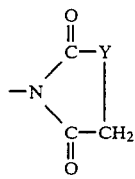

wherein Y is —NH—,

—O—, —S—, >CHOH, or —CH$_2$—O—; —S—R$^{10}$ wherein R$^{10}$ is selected from alkyl, alkyl substituted with one or more of halogen, hydroxy, phenoxy, aryl, cyano, cycloalkyl, alkylsulfonyl, alkylthio, alkanoyloxy, and alkoxy, phenyl, phenyl substituted with halogen, alkyl, alkoxy, alkanoylamino, cyano or alkoxycarbonyl, pyridyl, pyrimidinyl, 2-benzoxazolyl, 2-benzimidazolyl, 2-benzothiazolyl or

—SO$_2$R$^9$; —COOR$^9$; —OXR$^9$; —NH—X—R$^9$; —CONR$^{11}$R$^{11}$; —SO$_2$NR$^{11}$R$^{11}$; wherein R$^9$ and X are as defined above and R$^{11}$ is selected from H, alkyl, aryl, alkoxyaryl, cycloalkyl, amino, alkenyl, alkylamino, dialkylamino, arylamino, furyl, and alkyl substituted with one or more of halogen, hydroxy, phenoxy, aryl, cyano, cycloalkyl, alkylsulfonyl, alkylthio, alkanoyloxy, and alkoxy; alkoxy substituted with hydroxy, cyano or alkanoyloxy; alkoxyalkoxy substituted with hydroxy, cyano, alkanoyloxy or alkoxy; phenoxy substituted with 1-3 of alkyl, alkoxy or halogen;

R$^5$, R$^6$, R$^7$, and R$^8$ are each selected from hydrogen and alkyl; and wherein the above alkyl and alkylene portions of groups R$^1$ through R$^{11}$ contain 1-6 carbons.

Particularly useful herein are the amine reactants of the formulae:

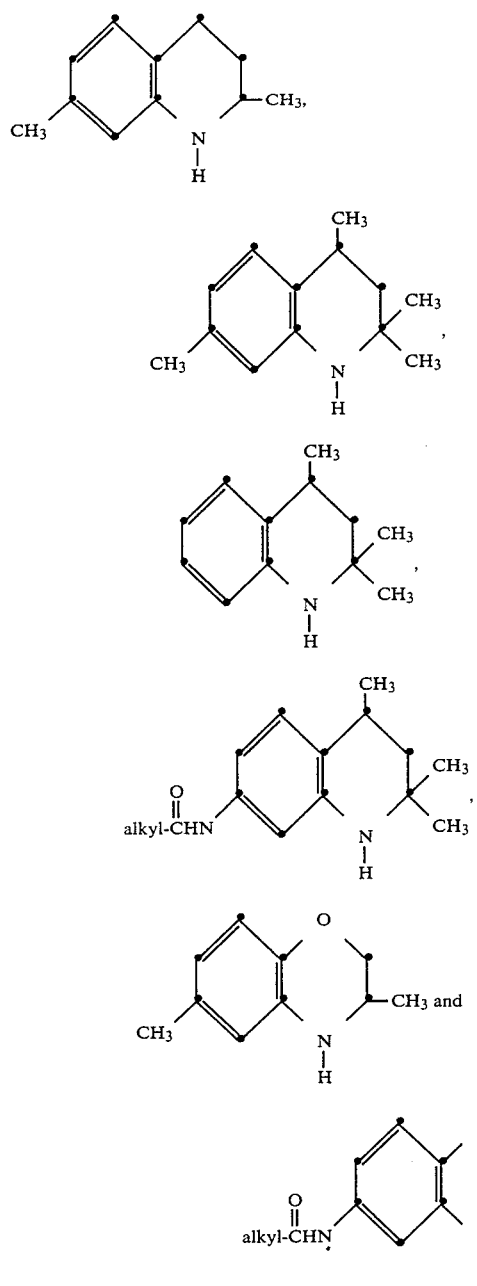

The following tables give further examples of useful amine reactants.

TABLE 1

| R¹ | R² | R³ |
|---|---|---|
| H | H | —CH₂CH₂OCOCH₃ |
| " | " | —CH₂CH₂CN |
| " | " | —CH₂CH₂OH |

TABLE 1-continued

| R¹ | R² | R³ |
|---|---|---|
| " | " | —CH₂CH₂—N(succinimide) |
| " | —CH₃ | —CH₂CH₂OCOC₆H₅ |
| " | " | —CH₂CH₂CH₂CH₃ |
| " | " | —CH₂C₆H₅ |
| " | " | —CH₂CHCH₂OH<br>       \|<br>       OH |
| " | " | —CH₂CH₃ |
| —CH₃ | " | —CH₂CH₂OH |
| " | " | —CH₂CH₃ |
| " | " | —CH₂CH₂OCOCH₃ |
| " | " | —CH₂CHCH₂OH<br>       \|<br>       OH |
| " | —OCH₃ | —CH₂CH₂CN |
| " | " | —CH₂CH₂Cl |
| —NHCOCH₃ | " | —CH₂CH₃ |
| " | " | —CH₂CH₂CN |
| " | " | —CH₂CH₂OCOCH₃ |
| " | —CH₃ | —CH₂CH₂CN |
| " | " | —CH(CH₃)CH₂CH₃ |
| H | —OCH₃ | —(thiophene) |
| —CH₃ | H | —CH₂CH₂SO₂NH₂ |
| —NHCOCH₃ | H | —CH₂—(furan) |
| " | " | —CH₂CH₂OCH₃ |
| " | " | —CHCH₃<br>    \|<br>    CH₂CO₂CH₂CH₃ |
| " | " | —CH—CH₂CH(CH₃)₂<br>    \|<br>    CH₂CH(CH₃)₂ |
| " | " | —CH₂CH(CH₂)₄CH₂OH<br>       \|<br>       OH |
| " | " | —CH(CH₃)—CH₂CH₃ |
| H | —CH₃ | —(thiophene) |
| H | H | CH₂CH₂CN |
| " | " | CH₃ |
| " | " | CH₂CH₃ |
| " | Cl | CH₂C₆H₅ |
| " | " | C₆H₁₁ |

TABLE 1-continued

[Structure: benzene ring with $R^2$ (ortho to N), $R^1$ (para to N), and NHR³ substituent]

| $R^1$ | $R^2$ | $R^3$ |
|---|---|---|
| —NHCOC$_2$H$_5$ | " | CH$_2$CH$_2$OH |
| " | —OCH$_3$ | CH$_2$CH$_2$OCOCH$_3$ |
| " | " | CH$_2$CH(OH)CH$_2$OH |
| " | " | CH$_2$CH$_2$CN |
| " | " | CH$_2$CH$_2$OCOCH$_3$ |
| " | " | CH$_2$CH$_2$OCOC$_6$H$_5$ |
| " | " | CH$_2$CH$_2$OCOCH$_3$ |
| Cl | " | CH$_2$CH$_2$CN |
| CH$_3$ | H | CH$_2$CH—CH$_2$OCOCH$_3$ <br> \| <br> OCOCH$_3$ |
| CH$_3$ | H | CH$_2$CH$_3$ |
| " | " | CH$_2$CH$_2$OH |
| " | " | CH$_2$CH$_2$NH$_2$ |
| NHCOCH$_3$ | " | CH$_2$CH$_3$ |
| " | " | CH$_2$CH$_2$OCOCH$_3$ |
| " | " | (CH$_2$CH$_2$O)$_2$CH$_2$CH$_3$ |
| NHCOC$_6$H$_5$ | " | CH$_2$CH$_2$CONH$_2$ |
| " | —CH$_3$ | CH$_2$CH$_3$ |
| NHCOCH$_3$ | —OC$_2$H$_5$ | " |
| " | " | CH$_2$CH$_2$OCOCH$_3$ |
| " | " | CH$_2$CH(OH)CH$_3$ |
| " | " | CH$_2$CH$_2$OH |
| " | —OCH$_3$ | CH$_2$CH$_2$OCOCH$_3$ |
| " | " | [thiophene-2-yl group] |
| " | H | CH$_2$CH$_2$OCNH—[phenyl] |
| " | " | 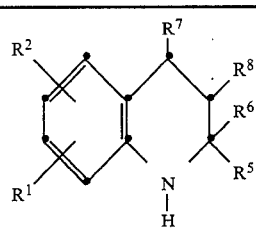 |

TABLE II

[Structure: tetrahydroquinoline with $R^1$, $R^2$ on benzene ring and $R^5$, $R^6$, $R^7$, $R^8$ on the saturated ring, NH]

$R^1$, $R^2$, $R^5$, $R^6$, $R^7$, $R^8$ 2,7-di-CH$_3$
2,5-di-CH$_3$—8-OCH$_3$
2,2,4,7-tetra-CH$_3$
2,2,4-tri-CH$_3$
2-CH$_3$—7-NHCOCH$_3$
2,2,4-tri-CH$_3$—7-NHCOCH$_3$
2-CH(CH$_3$)$_2$—7-NHCOCH$_3$
7-CH$_3$
3-CN—7-CH$_3$

TABLE II-continued

[Same structure]

$R^1$, $R^2$, $R^5$, $R^6$, $R^7$, $R^8$

3-CONH$_2$—7-CH$_3$
3-Cl—7-CH$_3$
3-OCH$_3$—7-CH$_3$
2,2,4-di-CH$_3$—5,8-di-OCH$_3$
2,2,4-tri-CH$_3$—8-OCH$_3$
3-OH—7-CH$_3$

TABLE III

[Structure: dihydrobenzoxazinone-type with $R^1$, $R^2$ on benzene, $R^5$ on ring, NH]

$R^1$, $R^2$, $R^5$ 3,6-di-CH$_3$
3-CH$_3$
3-CH$_3$—6-NHCOCH$_3$
6-NHCOCH$_3$
3-CH$_3$—6-Cl
6-NHCOC$_6$H$_{11}$
6-NHCOC$_6$H$_5$
6-NHCOOC$_2$H$_5$
6-NHCONHC$_2$H$_5$
6-NHCOCH(CH$_3$)$_2$
6-NHCOCH$_2$Cl
6-NHCOCH$_2$C$_6$H$_5$
6-NHCOCH$_2$OC$_6$H$_5$
6-NHCOCH$_2$CH$_2$Cl
6-NHCOCH$_2$CN
6-NHCOOC$_4$H$_9$—n
6-NHCOC$_6$H$_4$—p-OCH$_3$
6-NHCONHC$_6$H$_5$
6-OCH$_3$
6-OC$_4$H$_9$—n
6-Br

The efficiency of the present process depends greatly on the solvent employed, one or more in all proportions of ethylene glycol, propylene glycol and 2-ethoxyethanol, being preferred. Simple alcohol solvents such as alcohols, alcohol-water mixtures, dimethylformamide, and the like do not work satisfactorily for many of the reactants and result in markedly reduced yields. The ratio by weight of solvent to total reactants may be widely varied, e.g., between about 1 and 50, but preferably is between about 2 and 15.

In carrying out the process the molar ratio of sulfonate to arylamine is preferably at least one and most preferably from about 1.5 to about 3.0, although higher or lower ratios may be used, but to no significant advantage. The use of a base such as NaOH or KOH is not critical but most preferably should be present in amounts sufficient to neutralize acid as formed and thereby enhance the rate of reaction, although some acid is of course tolerable. It is preferred that a major portion (at least about half) of the acid be neutralized. As indicated above, the amount of solvent likewise is not critical but should be sufficient to maintain solution of the reaction medium and allow easy stirring thereof. The temperature of the reaction medium can vary between about 100° C. and 180° C., but preferably is between about 115° C. and 140° C., and most preferably from about 120° C., and 135° C.

The following example (Step B) further illustrates the present invention:

STEP A

A mixture of 67.8 g (0.66 mol) of NaHSO$_3$, 60.0 g of epichlorohydrin, and 135 ml of water was stirred at reflux at 7.0 hours and let cool to 22° overnight. Filtration afforded 72.3 g of sodium-2-hydroxy-3-chloro-1-propanesulfonate.

STEP B

A mixture of 10.0 g (0.05 mol) of the above sulfonate, 4.03 g (0.025 mol) of 2,7-dimethyl-1,2,3,4-tetrahydroquinoline, 3.29 g of 85% KOH (0.05 mol), and 80 ml of ethylene glycol was stirred at 120°–135° C. for six hours. The reaction mixture was cooled, diluted to 150 cc with water, and extracted with hexane to remove any unreacted tetrahydroquinoline derivative. The aqueous phase contained 0.0172 moles of product useful without further purification for in situ coupling in conventional manner to diazo components to give dyes such as

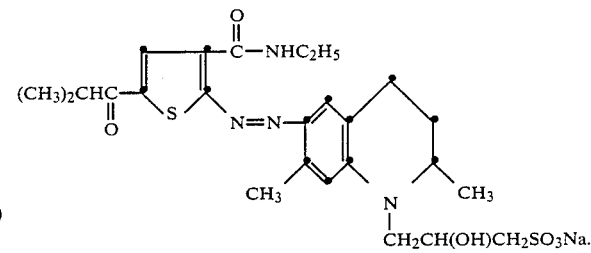

The invention has been described in detail with particular reference to preferred embodiments thereof, but it will be understood that variations and modifications can be effected within the spirit and scope of the invention.

We claim:

1. The process for preparing a compound of the formula

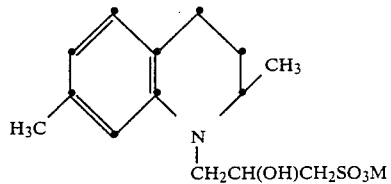

wherein M is NH$_4$+ or a group IA metal, comprising reacting at between 100° C. and 180° C., in ethylene glycol, a sulfonate of the formula X—CH$_2$CH(OH)CH$_2$SO$_3$M wherein X is halogen, with 2,7-dimethyl-1,2,3,4-tetrahydroquinoline.

* * * * *